Figure 1:
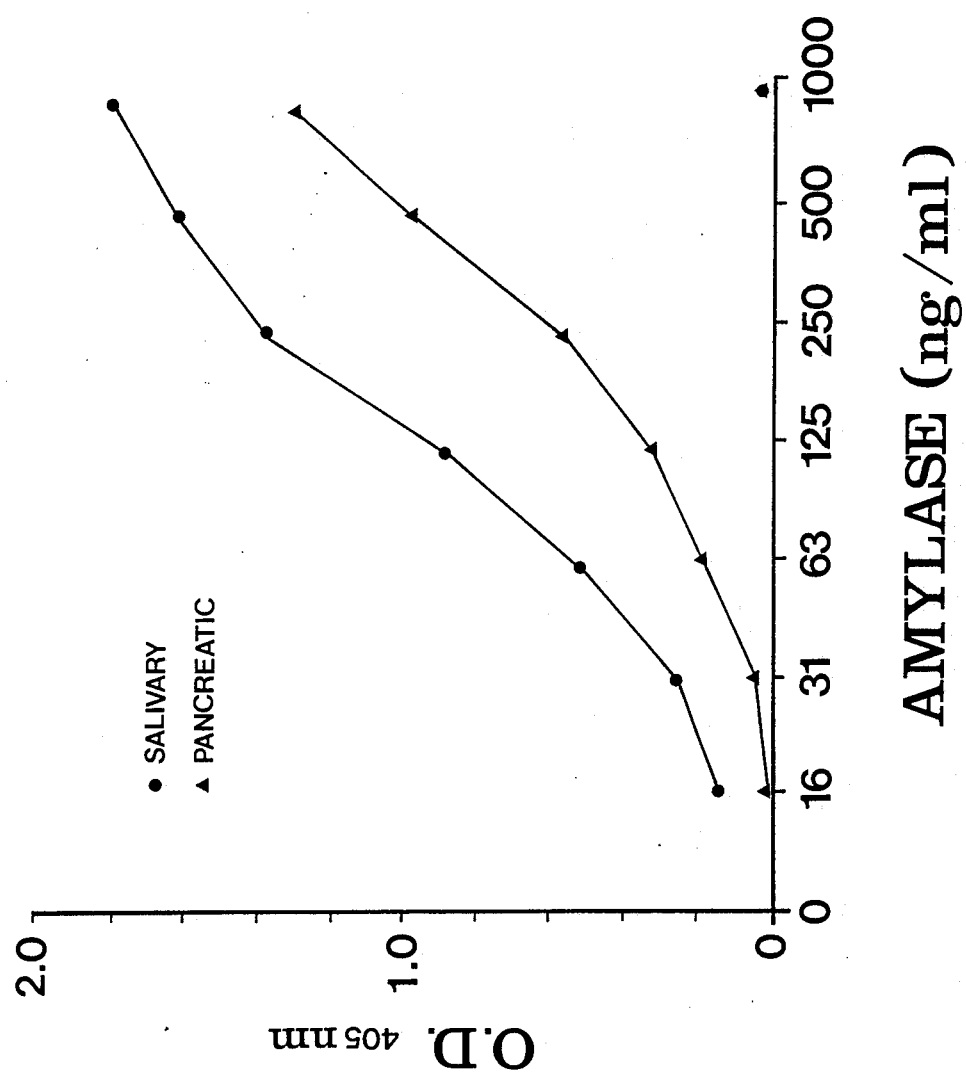

United States Patent [19]

Woodward

[11] Patent Number: 4,952,507
[45] Date of Patent: Aug. 28, 1990

[54] PRODUCTION AND DIAGNOSTIC USE OF ANTIBODIES AGAINST PANCREATIC ALPHA-AMAYLASE

[75] Inventor: Michael P. Woodward, Charlottesville, Va.

[73] Assignee: Humagen Incorporated, Boca Raton, Fla.

[21] Appl. No.: 327,404

[22] Filed: Mar. 21, 1989

Related U.S. Application Data

[63] Continuation of Ser. No. 896,040, Aug. 13, 1986, abandoned.

[51] Int. Cl.$^5$ .................. C12N 5/00; C12N 15/00
[52] U.S. Cl. ...................... 435/240.27; 435/172.2; 530/387; 530/845; 935/104
[58] Field of Search .............. 435/7, 172.2, 240.27; 530/387, 389, 845; 935/104

[56] References Cited

FOREIGN PATENT DOCUMENTS

35874 4/1984 Australia .
51722 2/1985 Australia .
52656 6/1986 Australia .
58-183098 10/1983 Japan .
60-106573 7/1986 Japan .

OTHER PUBLICATIONS

Urdal et al., "Macroamylase Immunoglobulins Show High Affinity for Animal and Human Amylases", Clinical Chemistry 31:699-703 (May 1985).
Hiroishi et al., "Differential Assay of Human Salivary and Pancreatic α-Amylase Using a Monoclonal Antibody Insolubilized on Bacterial Cell Wall", Clinica Chimica Acta 159:89-91 (Aug. 1986).
Gerber et al., "Inhibition of Human Saliva and Pancreas Amylase by Monoclonol Antibodies", Chemical Abstracts 106: #29347m, Eur. Pat. Appl. EP 194,600, 17 Sep. 1986, DE Appl. 3,508,384, 08 Mar. 1985 (2 Feb. 1987).
Bruns et al., Clin. Chem. 31(8):12867-1288 (1985).
M. Gerber et al., Clin. Chem. 32(6):1131 (1986).
T. E. Mifflin et al., Clin. Chem 31(8):1283-1286 (1985).
M. Gerber et al., Clin. Chem. 31(8):1331-1334 (1985).
K. Ito et al., J. Biochem. 97:1357-1362 (1985).

Primary Examiner—Christine M. Nucker
Assistant Examiner—Karen I. Krupen
Attorney, Agent, or Firm—Lieberman, Rudolph & Nowak

[57] ABSTRACT

Antibodies specific for pancreatic alpha-amylase and methods for their production are described. These antibodies may be used for the detection and quantification of pancreatic alpha-amylase in biological fluids, tissue extracts, or extracts of stains of biological fluids.

2 Claims, 1 Drawing Sheet

PRODUCTION AND DIAGNOSTIC USE OF ANTIBODIES AGAINST PANCREATIC ALPHA-AMAYLASE

This is a continuation of U.S. application Ser. No. 896,040, filed Aug. 13, 1986.

This invention relates to the production and use of antibodies that are specific for the isoenzyme, pancreatic alpha-amylase (hereinafter referred to as PAM).

As a routine procedure, serum amylase ($\alpha$-1,4glucan 4-glucanohydrolase E.C. 3.2.1.1) is assayed to assist in the diagnosis of abdominal pain. Normal amylase assays are determinations of enzymatic activities, i.e., the rate of hydrolysis of $\alpha$-1,4-glycosidic bonds. They are non-specific for PAM because there are several amylase isoenzymes. Therefore, it is highly useful to be able to differentiate the isoenzymes in patients with hyperamylasemia and, more particularly, in patients with hyperamylasemia of unknown etiology.

Various immuno-techniques have been devised in the hope of providing the desired differentiation. Generally, conventional immuno-techniques have been singularly unsuccessful. This is because most clinically and forensically significant samples contain both PAM and the salivary-type alpha-amylase. Conventional antisera obtained by immunization with intact PAM usually crossreact with the salivary alpha-amylase. In principle, monospecific antisera can be prepared by absorption but preparations of such antisera are tedious and costly. In addition, one preparation is different from another in titer and avidity against the antigen. The problem of crossreactivity is a serious one. For example, total normal serum amylase activity varies from about 40 to about 120 units per liter. PAM accounts for about half the total activity, as does the salivary enzyme. Even pathological changes in the level of PAM can be missed in a test wherein the immunoreagent used to detect PAM crossreacts with the salivary enzyme appreciably. Therefore, a preferred immunoreagent should have no more than about 0.5% crossreactivity against the salivary-type alpha-amylase. A highly preferred immunoreagent should have less than about 0.10% crossreactivity against the salivary-type alpha-amylase.

There are many ways to measure crossreactivity of an immunoreagent. For the purpose of this application, crossreactivity is defined below in Example 9. For the purpose of this application, an immunoreagent specific against PAM is an immunoreagent which is reactive to PAM and which has less than 1%, and more preferably less than 0.1% crossreactivity with the salivary type alpha-amylase. Where greater certainty is desired, the more stringent standard should be applied.

The present invention provides such preferred immunoreagents. In a preferred embodiment of this invention, monoclonal antibodies specific against PAM are prepared and used. Either singly or in combination, these monoclonal antibodies are capable of specifically reacting with PAM from any biological sample. Hence, they are novel diagnostic reagents for the detection and quantification of PAM in samples containing mixtures of PAM and other alpha-amylases.

The immunoreagents of this invention may be used in human medicine, veterinary medicine, forensic medicine, or in research for diagnostic and analytical purposes, and for PAM purification.

The invention also provides a method for repeatedly producing large quantities of immunoreagents specific against PAM of consistent quality that can serve as highly sensitive and specific probes in medical and veterinary diagnosis or research. The potential clinical and commercial importance of these antibodies, particularly in the human and animal immunodiagnostics area, is very great.

The technique for producing monoclonal antibodies was pioneered in the mid-1970's by Kohler and Milstein who successfully fused antibody-producing spleen lymphocytes that had been sensitized with sheep red blood cells with malignant cells (myelomas) of bone marrow primary tumors [Milstein, Sci. Am. 243:66 (1980)]. The method was used to create antibody-producing hybrid cell lines from single fused cell hybrids, or monoclones. Each monoclone (also called a hybridoma) secreted a monoclonal antibody, i.e., a single type of immunoglobulin, directed against the sheep red blood cell antigen that had been used to sensitize the parental spleen lymphocyte. Moreover, like the parental myeloma cell line, the monoclones had indefinite lifespans in tissue culture and in vivo.

Monoclones and monoclonal antibodies can also be produced by other hybridoma techniques, such as the human B-cell hybridoma technique disclosed in Kozbor et al., 1983, Immunology Today 4:72; and the Epstein Barr Virus (EBV)-hybridoma technique disclosed in Cole et al., 1985, Monoclonal Antibodies and Cancer Therapy, Alan R. Liss, Inc., pp. 77-96 and the like. The Kozbar et al. article and the Cole et al. article are incorporated herein by reference.

The use of monoclonal antibodies has had a major impact in the fields of immunological research and medicine where conventional antisera have previously been used. While antisera derived from vaccinated animals are variable mixtures of antibodies which can never be reproduced precisely, a monoclonal antibody is a single species of immunoglobulin. The immunoglobulin secreted by a monoclone is directed against a single antigenic determinant on the antigen against which the immunogolobulin was produced. [Benjamin et al., Ann. Rev. Immunol. 2:67 (1984)]. Therefore, even though all of the antibody molecules produced by a given monoclone will be identical, a number of different monoclonal antibodies may be raised against the several antigenic determinants of a given antigen. Monoclones can be reproduced indefinitely and are easily propagated in vitro or in vivo. Moreover, they yield monoclonal antibodies in extremely high concentrations.

Monoclonal antibody production methods have broad utility, and they have been used to produce antibodies to many antigens. For instance, it has been reported that monoclonal antibodies have been raised against tumor cells (Koprowski, et al. U.S. Pat. No. 4,172,124), viruses (Koprowski et al, U.S. Pat. No. 4,196,265), and Group B Streptococci [Polin, Monoclonal Antibodies Against Streptococcal Antigen, pp. 353-359, in R. Kennet et al. (editors), Monoclonal Antibodies, Hybridomas: A New Dimension in Biological Analysis, Plenum Press, New York (1980)].

It is believed that until this invention no polyvalent or monoclonal antibodies have been produced that are specific for pancreatic alpha-amylase, i.e., do not appreciably crossreact with salivary-type alpha-amylase. Furthermore, it appears that pancreatic alpha-amylase-specific antibodies have heretofore not been utilized in the diagnosis of human or animal disease; nor have such antibodies been used in the detection and quantification of alpha-amylases in forensic specimens.

The connections between various diseases and total alpha-amylase activity in the body as determined by clinical laboratory tests have been documented in Friedman, R.B., et al., Clin. Chem. 26:1D, (1980). This paper presents a non-selective, extensive, listing of diseases compiled from the medical literature, that show altered amylase activity in a wide variety of biological fluids, and is hereby incorporated by reference.

Elevation of total alpha-amylase level in the body is usually indicative of disease. To help determine the particular amylase which is responsible for this change, the present invention provides novel means and method for detecting and quantifying PAM in samples, for diagnosing various diseases in animals and in human beings, and for forensic and research purposes.

The present invention provides continuous cell lines which produce monoclonal antibodies specific against PAM, comprising, for each such cell line: a monoclone of a hybrid of a cell capable of producing an antibody specific against PAM and a myeloma cell. The present invention also provides immunoreagents specific against PAM, including monoclonal antibodies specific against PAM.

In a preferred embodiment there is additionally provided one or more of the following features:
  (a) the PAM used as antigen is of human origin;
  (b) the cell capable of producing an antibody specific against PAM is a spleen cell or a lymph node cell, and more preferably also a B-lymphocyte;
  (c) the myeloma cell is a mouse myeloma cell or, more preferably, a "non-producing" mouse myeloma cell;
  (d) the cell capable of producing an antibody specific against PAM is obtained by in vitro sensitization of cells capable of producing antibodies with PAM or an immunogenic fragment thereof, or obtained from an animal, more preferably, a mouse, immunized with PAM or an immunogenic fragment thereof. In one example, the cell capable of producing an antibody specific against PAM is a A/J mouse B-lymphocyte and the myeloma cell is a mouse "non-producing" myeloma cell.

The present invention also provides a method for testing for PAM. The method comprises: contacting an immunoreagent specific against PAM with a sample suspected to contain PAM, and detecting the interaction of the immunoreagent with PAM in the sample.

In a preferred embodiment, there is additionally provided one of more the following features:
  (a) the sample is a forensic specimen, or a biological sample. The biological sample may be serum, urine, saliva, ascites fluid, pleural fluid, tissue extract, semen, seminal fluid or the like. It may also be an extract of a stain of a biological fluid. The biological fluid may be blood, urine, saliva, semen, seminal fluid or the like;
  (b) the immunoreagent is a-monoclonal antibody or a mixture of monoclonal antibodies; and
  (c) the detection of the interaction of the immunoreagent with PAM in the sample is a detection of immuno-complexes.

The detection of the interaction of the immunoreagent with PAM in the sample can be achieved in numerous ways. The forms of detection include but are not limited to detection of immunocomplexes by radioimmunoassay, enzyme-linked immunoassay, immunoblot assay, sandwich (two site) assay, immunoabsorbent assay, indirect immunoassay and the like. These and other standard forms of practice are well known to a person of ordinary skill in the art of immunodiagnostics, and are fully embraced by the present invention.

Furthermore, methods of detection based on the enzymatic activity of PAM are also within the scope of this invention.

Therefore, in another embodiment, an immunoreagent is used to remove specifically PAM but not other alpha-amylases from a sample. The total free alpha-amylase activity in the sample is measured both before and after the removal. The activity in the sample due to PAM is the difference between the two measurements. Alternatively, the alpha-amylase activity bound to the immunoreagent is measured to determine PAM in the sample. Moreover, the alpha-amylase activity remaining in the sample is the sum total of all other alpha-amylase activities. The specific removal of PAM can also serve as a convenient means for PAM purification. Preferably, the sample is a fluid. Preferably, the immunoreagent is a monoclonal antibody or a mixture of monoclonal antibodies, and attached to a solid support. More preferably the sample is a fluid and the immunoreagent, a monoclonal antibody or a mixture of monoclonal antibodies, is attached to a solid support.

The invention will be described in further detail in conjunction with FIG. 1, which demonstrates specificity of a representative monoclonal antibody specific against PAM and its non-reactivity with salivary alpha-amylase.

Pancreatic alpha-amylase (PAM) is a protein having approximately 512 amino acids which is produced by the pancreas and is a α-1,4-glucan, 4-glucanohydrolase. PAM can be purified from homogenates of human pancreas by, for example, a modification of the technique described by Zakowski and Bruns [Zakowski, J.J., Gregory, M.R., and Bruns, D.E. Clin. Chemistry 30:62 (1984)]: Human pancreatic tissue is shredded and then homogenized in 150 mM NaCl, pH 6.9, containing 50 mM glycerophosphate, 0.01% NaN$_3$, 0.32 mg/ml phenylmethylsulfonyl fluoride (PMSF), 0.01 mg/ml aprotinin. The homogenate is centrifuged for 20 minutes at 10,000×g and the resulting supernatant is then centrifuged for 100 minutes at 100,000×g. The latter supernatant is then applied to a CHA-Sepharose (cyclohexoamylose-Sepharose) column equilibrated in a buffer containing 50 mM NaPO$_4$, 50 mM NaCl, 0.01% NaN$_3$, and 0.01 mg/ml aprotinin, pH 6.9 (3NA buffer). Following extensive washing with this buffer to remove extraneous protein the PAM is eluted with 3NA buffer containing 0.8% cyclohexoamylose. PAM can also be prepared from other animals by this technique.

PAM is used to immunize animals, such as mice, rats, horses, sheep, pigs, frogs, rabbits, etc., to obtain antibody producing somatic cells for fusion to myeloma cells.

Immunogenic fragments of PAM, by themselves or coupled to a carrier molecule, for example, bovine serum albumin, can also be used for immunization. Coupling techniques are well known in the art.

Somatic cells with the potential for producing antibodies, particularly B-cells, are suitable for fusion with a myeloma cell line. These somatic cells may be obtained from the lymph nodes, spleens and peripheral blood of primed animals. In a preferred embodiment of this invention mouse spleen cells are used, in part because mouse lymphocytes produce a relatively high percentage of stable fusions with mouse myeloma lines.

It would be possible, however, to use rat, rabbit, frog, horse, sheep, pig or other cells instead.

Specialized myeloma cell lines have been developed from lymphocyte tumors for use in hybridoma-producing fusion procedures [Kohler and Milstein, Eur. J. Immunol. 6:511 (1976); Shulman et al., Nature 276:269 (1978); Volk et al., J. Virol. 42:220 (1982)]. These cells lines have been developed for at least three reasons. The first for using these cell lines is to facilitate the selection of fused hybrids from unfused and similarly immortal myeloma cells. Usually, this is accomplished by using myelomas with enzyme deficiencies that render them incapable of growing in certain selective media, which media support the growth of fused hydrids. The second reason arises from the inherent ability of many myeloma cells to produce their own antibodies (myeloma proteins). The purpose of using monoclonal techniques is to obtain fused hybrid cell lines with unlimited lifespans that produce the desired single antibody under the genetic control of the "somatic cell" component of the monoclone. To eliminate the production of tumor cell antibodies (myeloma proteins) by the monoclones, "non-producing" myeloma cell lines incapable of producing or secreting immunoglobulins are used. A third reason for selection of these cell lines is for their suitability and efficiency for fusion.

Several myeloma cell lines have thus been used for the production of fused cell hybrids, including P3/X63-Ag 8, P3/NSI/1-Ag 4-1, Sp2/0-Ag-14 and S194/5.XXOBU.1. The P3/X63-Ag 8 and P3/NSI/1-A.G 4-1 cell lines have been described by Kohler and Milstein, Eur. J. Immunol. 6:511, (1976). Shulman et al., Nature 276:269 (1978) developed the Sp2/0-Ag-14 myeloma line. The S194/5.XXOBU.1 line was reported by Trowbridge, J. Exp. Med. 148:313 (1979). In the example of the present invention, infra, the Sp2/0-AG-14 line, a nonproducing myeloma cell line derived from BALB/c mice, is preferred. All of the above identified myeloma cell lines are available to the public through American Type Culture Collection (Rockville, Md.).

Human myeloma cells can also be used in the present invention. See, e.g., Kozlor et al., 1983, Immunology Today 4:72. Moreover, because a critical function provided by the "myeloma cell" component of the hybrid is the immortality function, such immortal cell lines as EBV transformed cells of the B-cell lineage will do as well. Therefore, for the purpose of this application, myeloma cells are to be broadly construed to include the immortal EBV transformed B-cells; and the human hybridoma technique and the EBV-hybridoma technique are within the scope of the present invention.

Methods for generating hybrids of antibody-producing somatic cells and myeloma cells usually involve mixing somatic cells with myeloma cells in a 10:1 proportion (though the proportion may vary from 20:1 to 1:1), in the presence of an agent or agents, (chemical, viral or electrical) that promote the fusion of cell membranes. It is preferred that the same species of animal serve as the source of the somatic and myeloma cells used in the fusion procedure. Intraspecies hydrids are genetically more stable than interspecies hydrids. Fusion methods have been described [by Kohler and Milstein, Nature 256: 495 (1975) and Eur. J. Immunol. 6:511 (1976), by Gefter et al., Somatic Cell Genet. 3: 231 (1977), and by Volk et al. J. Virol. 42: 220 (1982).] The fusion-promoting agents used by these investigators were inactivated Sendai virus or polyethylene glycol (PEG). The fusion procedure of the example of the present invention, infra, is that described by Volk et al., supra, in which PEG is added to the mixture of mouse spleen and myeloma cells to promote the formation of fused cell hybrids.

Because fusion procedures produce viable hybrids at very low frequency (e.g., when spleens are used as a source of somatic cells, only one hybrid is obtained for roughly every $1 \times 10^5$ spleen cells), it is essential to have a means of selecting the fused cell hybrids from the remaining unfused cells, particularly the unfused myeloma cells. A means of detecting the desired antibody-producing hybridomas among other resulting fused cell hybrids is also necessary.

Generally, the selection of fused cell hybrids is accomplished by culturing the cells in media that support the growth of hybrids but prevent the growth of the myeloma cells which normally would go on dividing indefinitely. (The somatic cells used in the fusion do not maintain viability in in vitro culture and hence do not pose a problem.) In the example of the present invention, myeloma cells lacking hypoxanthine phosphoribosyl transferase (HPRT-negative) were used. Selection against these cells is made in hypoxanthine/aminopterin/thymidine (HAT) medium, a medium in which the fused cell hybrids survive due to the HPRT-positive genotype of the spleen cells. The use of myeloma cells with other genetic deficiencies (drug sensitivities, etc.) that can be selected against in media which support the growth of hybrids is also possible.

Several weeks are required to selectively culture the fused cell hybrids Early in this time period, it is necessary to identify those hybrids which produce the desired antibodies so that they may subsequently be cloned and propagated. Generally, around 10% of hybrids obtained produce the desired antibodies, although a range of from 1 to 30% is not uncommon. The detection of antibody-producing hybrids can be achieved by one of several standard assay methods, including enzyme-linked immunoassay and radioimmunoassay techniques which have been described in the literature. See, e.g., Kennet et al. (editors), Monoclonal Antibodies and Hybridomas: A New Dimension in Biological Analyses, pp. 376–384, Plenum Press, New York (1980). The detection method used in the example of the present invention was an enzyme-linked immunoassay employing a peroxidase-conjugated anti-mouse immunoglobulin.

Once the desired fused cell hybrids have been selected and cloned into individual antibody-producing cell lines, each cell line may be propagated in either of two standard ways. A suspension of the cells can be injected into a histocompatible animal. The injected animal will then develop tumors that secrete a PAM specific monoclonal antibody produced by the fused cell hybrid. The body fluids of the animal, such as serum or ascites fluid, can be tapped to provide the monoclonal antibody in high concentration. Alternatively, the individual cell lines may be propagated in vitro in laboratory culture vessels. Culture medium containing high concentrations of specific monoclonal antibody or antibodies can be harvested by decantation, filtration or centrifugation.

Immunoreagents specific against pancreatic alpha-amylase (PAM) can be used to detect PAM. Accordingly, this invention provides a method for testing for PAM comprising: contacting an immunoreagent specific against PAM with a sample suspected to contain the amylase, and detecting the interaction of the immunoreagent with the amylase in the sample. In a preferred embodiment, the sample is a biological sample, such as serum, urine, saliva, ascites fluid, pleural fluid, tissue extract semen, seminal fluid and the like, and stains of the same. In another preferred embodiment, the immunoreagent is a monoclonal antibody or a mixture of monoclonal antibodies. In a more preferred embodiment the sample is a biological sample and the immunoreagent is a monoclonal antibody or a mixture of monoclonal antibodies. This more preferred embodiment is clinically useful in alpha-amylase isozyme differentiation in patients with hyperamylasemia, e.g. patients with acute or chronic pancreatitis, secondary malignant neoplasms with carcinomatous peritonitis, pancreatic cyst and pseudocyst, diabetes mellitus, protein malnutrition, cirrhosis of the liver, malignant neoplasms of bronchus and lung, diabetic acidosis, and possibly patients undergoing pancreas rejection following transplantation.

In each of the above embodiments, numerous techniques can be used to detect the interaction of the interaction of the immunoreagent with the amylase in the sample. The techniques are well known to the skilled person in the art of immunodiagnostics. Some of these are indicated below for the purpose of illustration only and not of limitation.

The immunoreagent of this invention may be in soluble form or attached to a solid support. In a preferred embodiment, the immunoreagent is attached to a solid support. Useful solid supports include but are not limited to nitrocellulose filters and the like; to plastic beads, Sepharose (tradename for a beaded agarose produced by Pharmacia Fine Chemicals, Piscataway, N.J.), polyacrylamide beads and the like, plastic test tubes, plastic ELISA-assay plates such as Immunlon II plates (Dynatech Laboratories, Inc., Chantilly, VA 22021) and other similar multi-well plates. The details for attaching antibodies to a solid support are not described because such attachment procedures are amply provided in the literature and basic texts. The attachment may be by covalent linkage, non-covalent linkage and as-yet-not-understood linkage to the solid support. The artisan of ordinary skill in the art will know these procedures or will be able to follow these readily available procedures or make standard modifications thereof.

An example of this embodiment is where the immunoreagent is attached to a solid support. Contact of this immunoreagent coated support with a fluid containing PAM would result in the binding of PAM to the immunoreagent support. The support is removed from the fluid or vice versa, and washed. After washing the bound PAM can be detected by a second immunoreagent that binds PAM and which has a signal generating moiety. The signal generating moiety can be a radioactive moiety, a electron-dense moiety, a detectable chemical moiety, a catalytic moiety or a luminescent moiety. Of course, it is imperative that the first and second immunoreagents not share a single, mutually exclusive binding site to PAM.

The above example is an example of a "sandwich" assay, which involves an antigen and two antibodies in one order or another. More generally, this is an immunoassay.

Alternatively, in lieu of a second immunoreagent, the bound PAM can be detected by its own enzymatic activity. Therefore, after washing, the bound PAM is contacted with a substrate under catalytic conditions and catalysis of the substrate is monitored.

The details of an alpha-amylase assay are not herein described because such procedures are well known to the skilled artisan or, at any rate, readily available from standard texts and other sources. For example, alphaamylase activity can be measured by a coupled-enzyme method, using maltotetraose as the substrate. This method has been described in Whitlow, et al., Clin. Chem., 25: 481–483 (1979). The paper of Whitlow et al. is incorporated herein by reference.

In another preferred embodiment, the sample is attached to a solid support. The immunoreagent specific against PAM has a signal generating moiety. Again, the signal generating moiety can have any of the forms disclosed supra. An example of this embodiment is where the sample is a tissue section fixed on a slide. A radioactive immunoreagent is contacted with the sample. After washing, the slide is processed for autoradiography.

Additionaly, purified PAM can be subjected to limited proteolysis by a number of proteinases which cleave peptide bonds at specific sites. PAM-specific proteolytic fragments can be isolated by using monoclonal antibodies specific against PAM. These fragments can be used to immunize animals and generate further preferred immunoreagents specific against PAM.

EXAMPLE 1

Hyperimmunization

To obtain spleen cells which produce antibodies to purified PAM, A/J mice were hyperimmunized with PAM. The mice were given an initial intraperitoneal injection with 100 μg of the antigen in 0.3 ml of 50 volume percent complete Freund's adjuvant in phosphate buffered saline (PBS; 10 mM phosphate, 150 mM sodium chloride, pH 7.2). Subsequent injections were made at two week intervals with 100 micrograms of PAM in 0.3 ml PBS mixed 1:1 (v/v) with incomplete Freund's adjuvant. A final injection of 100 μg of antigen in 0.1 ml of PBS was given intravenously 4 days later. In some cases an alternative method was used in which the peritoneal wall was opened and a final injection containing 100 μg of antigen in 0.1 ml of PBS was given directly into the spleen. Three to four days after the final intravenous or intrasplenic injection, the mice were sacrificed and their spleens were aseptically removed and used as described below.

Other immunization schedules may be used with similar success.

EXAMPLE 2

Spleen Cell Preparation

Spleens of hyperimmunized A/J mice were removed under sterile conditions and washed in RPMI-1640 serum-free medium (M.A. Bioproducts, Walkersville, MD). The spleens were macerated using 19 gauge needles attached to 1.0 ml tuberculin syringes. The cells were resuspended in RPMI-1640 medium (10–50 ml per spleen) and centrifuged. The supernatant fraction was removed and the spleen cells were resuspended in RPMI-1640 serum-free medium. The cell number was determined by microscopic hemacytometer count before mixing with myeloma cells.

Normal spleen cells may first be prepared as described, cultured and then sensitized by the antigen in vitro. Sensitization induces selective proliferation of lymphocytes which bear immunoglobulins directed against PAM. This is an alternative to in vivo sensitization as described.

EXAMPLE 3

Myeloma Cell Preparation

BALB/c mouse myeloma cells of the SP2/0-Ag-14 cell line (a HPRT-negative, 6-thioguanine resistent, nonproducing line) were maintained at 37° C. in a 7% carbon dioxide atmosphere in RPMI-1640 medium containing 10% fetal calf serum (FCS) and 2 μg/ml 6-thioguanine, supplemented with 50 μg/ml gentamycin. The myeloma cells were maintained in the log growth phase with cell density never exceeding about $2 \times 10^5$ cells/ml. Before cell fusion, the myeloma cells were washed by centrifugation in RPMI-1640 serum-free medium, resuspended in the same medium and counted.

EXAMPLE 4

Fusion of Spleen and Myeloma Cells to Produce Hybrids

After the spleen and myeloma cells were washed in RPMI-1640 serum-free medium and counted, they were mixed in V-bottom 50 ml plastic tubes. About $1 \times 10^8$ spleen cell were used. The ratio of spleen cells to myeloma cells in the mixture was 5:1. The cell suspensions were centrifuged at 250×g for 10 minutes at room temperature. After carefully aspirating all of the supernatant medium, the cell pellets were gently loosened from the bottom of the tube by tapping. The mixture of the spleen and myeloma cells was then suspended for one minute by stirring in 0.5 ml of a solution containing 35% (v/v) PEG and 65% (v/v) RPMI-1640 serum-free medium. To this cell suspension, 5 ml of RPMI-1640 serum-free medium was added dropwise over approximately a period of 3 minutes with constant, gentle agitation of the tube. A second 5 ml volume of RPMI-1640 serum-free medium was quickly added, and the cell suspensions were centrifuged as described above.

The pellets were resuspended in 20 ml of RPMI1640 serum-free medium, transferred to a 100 mm diameter plastic petri dish and incubated at 37° C. in a 7% carbon dioxide atmosphere for 30 minutes. The suspension of fused cells was then divided equally into two 50 ml plastic tubes, centrifuged as described above and diluted to a total volume of 80 ml with RPMI-1640 medium containing 10% FCS. The fused cells were plated into the wells of eight 96-well microtiter culture plates (Costar, Cambridge, MA) and the plates were incubated for 16 hours at 37° C. in a 7% carbon dioxide atmosphere. An equal volume of RPMI-1640 medium containing 10% FCS and 100 μM hypoxanthine, 50 nM aminopterin and 16 μM thymidine (HAT medium) was then added. Because this medium is selective for fused hybrids, hybrids will grow while unfused spleen and myeloma cells die. (Littlefield, Science, 145: 709 (1964)).

EXAMPLE 5

Selection of Fused Cells

After cell fusion, the plates were cultured for 2 to 4 weeks to allow for the outgrowth of hybrid cells. Periodically, about half of the HAT medium in the wells of the microtiter plates was removed and replaced with fresh HAT medium. After about 2-3 weeks, the medium was replaced with HAT-free medium, and screening was carried out.

EXAMPLE 6

Screening for Antibody-Producing Hybrids

An enzyme-linked immunoassay was used to screen fused cells for antibody production. The wells of 96-well microtiter plates were coated with 0.1 ml of PAM antigen (10 μg/ml in 50 mM Tris with 150 mM NaCl, pH 7.5) or the same amount of salivary alpha-amylase, for two hours at room temperature. The plates were then emptied, the wells filled with a solution containing 0.05% Tween 20 (polyoxethylene sorbitan monolaurate), 50 mM Tris, 150 mM NaCl, pH 7.5, (TTN buffer) and let stand for 30 minutes. The buffer was then removed and the plates washed three times with TTN buffer. [H. Friedman (editor), Manual of Clinical Immunology, pp. 506-512 (1976)]. After washing, 0.1 ml of culture fluid was taken from each of the wells of the microtiter plates in which the fused cells had been cultured and delivered to the wells of the microtiter assay plates. The plates were incubated for 60 minutes at room temperature to allow antibody binding to occur and then washed five times with the Tween 20 buffer.

To detect bound antibodies, 0.1 ml of peroxidase-conjugated goat anti-mouse IgG (heavy and light chain specific) immunoglobulin (Hyclone Laboratories, Logan, Utah) diluted 1:6000 in Tween 20 buffer was added to the microtiter wells. The plates were allowed to stand for 60 minutes at room temperature and were washed 5 times with Tween buffer thereafter. Substrate solution (0.1 ml containing 25 mM citrate and 50 mM dibasic sodium phosphate buffer, pH 5.0, with 40 mg of orthophenyl diamine and 40 μl of 30% $H_2O_2$/100 ml of buffer) was added to the wells, and the plates were allowed to stand for 15 minutes at room temperature. Positive wells were noted, and the cells that had produced positive samples with PAM antigen but not with the salivary enzyme were cloned. Two wells out of 3 to 4 thousand in which the fused cells had been cultured contained hybrids which secrete antibodies specific against PAM.

EXAMPLE 7

Limiting-Dilution Cloning

Cloning was performed by counting the cells, diluting them in RPMI-1640 medium containing 10% FCS to a cell concentration of one cell per 0.1 ml and adding 0.1 ml of the diluted cell suspension to new microtiter wells. After 2-4 weeks of culturing (during which time the growth medium was replenished periodically and any seeded unfused spleen cells lost viability), hybrid clones appeared in the microtiter wells. The clones were rescreened for antibody production using the enzyme-linked immunoassay system as described above and those clones which produced antibodies against PAM were propagated.

EXAMPLE 8

Propagation of Hybrid Cells and Antibody Production

After the clones had grown to confluence in the microtiter plates they were transferred to 175 $cm^2$ culture flasks and cultured to a cell density suitable for injection into mice (about $5 \times 10^6$ cells per injection). Syngeneic (histocompatible) mice were injected with doses of cells from individual clones, and after the development of noticeable ascites tumors, the mice were tapped. The ascites fluid generally contained anti-PAM monoclonal antibodies in concentrations that were high enough that the fluid could be diluted $10^5$-fold and still produce a positive reaction in the enzyme-linked immunoassay system.

EXAMPLE 9

Specificity and Crossreactivity of Immunoreagents

A monoclonal antibody specific against PAM and one specific against salivary alpha-amylase were attached to separate wells of a plastic microtiter plate. Solutions containing various amounts of purified PAM or salivary alpha-amylase were added to wells coated with antibody. After a period of incubation, the wells were washed and the bound enzyme was detected by adding Pantrak Amylase Test Reagent, Behring Diagnostics, La Jolla, as substrate. The catalysis was conducted at 20° C. for 120 minutes generating a color the 405 nm-absorbance of which was determined.

Absorbance at 405 nm was plotted against the concentration of enzyme added to the well. The results are shown in FIG. 1 which illustrates the specificity of a monoclonal antibody specific against PAM, and its lack of cross-reactivity with the salivary type alpha-amylase. More specifically, this figure shows that each antibody specifically trapped only its cognate antigen. Thus, the monoclonal antibody specific against PAM trapped PAM (curve with triangles). The monoclonal antibody against salivary alpha-amylase trapped only the salivary type enzyme (curve with circles). Neither antibody bound the "non-cognate" enyzme (spot at the bottom right of the plot).

Crossreactivity of an immunoreagent against PAM with salivary alpha-amylase is measured by (Absorbance generated at 10,000 ng/ml salivary alpha-amylase minus Background Absorbance) divided by (Absorbance generated at 10,000 ng/ml PAM minus Background Absorbance) under the conditions set forth above.

At an enzyme concentration of 10,000 ng/ml (data not shown), there is no detectable crossreactivity of the monoclonal antibody specific against PAM with salivary alpha-amylase, although a 0.05% cross-reactivity can be detected experimentally.

The monoclonal antibody is produced by the monoclone RAll, which monoclone has been deposited on July 29, 1986 with the American Type Culture Association, Rockville, Md. and has been assigned accession number HB9154. The present invention is not to be limited in scope by the monoclone deposited, since the deposited embodiment is intended as a single illustration of one aspect of the invention. Indeed, many variations of this invention as herein set forth may be made without departing from the spirit and scope thereof. The specific examples described are given by way of illustration only, and the invention is limited only by the terms of the appended claims.

I claim:

1. The cell line designated, ATCC HB 9154.
2. The monoclonal antibody produced by the cell line of claim 1.

* * * * *